(12) United States Patent
Kristoffersen et al.

(10) Patent No.: US 10,874,373 B2
(45) Date of Patent: *Dec. 29, 2020

(54) METHOD AND SYSTEM FOR MEASURING FLOW THROUGH A HEART VALVE

(71) Applicant: General Electric Company, Schenectady, NY (US)

(72) Inventors: Kjell Kristoffersen, Oslo (NO); Sevald Berg, Horten (NO)

(73) Assignee: General Electric Company, Schenectady, NY (US)

(*) Notice: Subject to any disclaimer, the term of this patent is extended or adjusted under 35 U.S.C. 154(b) by 717 days.

This patent is subject to a terminal disclaimer.

(21) Appl. No.: 15/453,223

(22) Filed: Mar. 8, 2017

(65) Prior Publication Data

US 2017/0172538 A1    Jun. 22, 2017

Related U.S. Application Data

(63) Continuation of application No. 11/412,614, filed on Apr. 27, 2006, now Pat. No. 9,612,142.

(51) Int. Cl.
*A61B 8/06* (2006.01)
*A61B 8/00* (2006.01)
(Continued)

(52) U.S. Cl.
CPC ............ *A61B 8/065* (2013.01); *A61B 8/06* (2013.01); *A61B 8/0883* (2013.01); *A61B 8/145* (2013.01); *A61B 8/463* (2013.01); *A61B 8/466* (2013.01); *A61B 8/469* (2013.01); *A61B 8/488* (2013.01); *A61B 8/523* (2013.01); *A61B 8/5223* (2013.01);
(Continued)

(58) Field of Classification Search
CPC ......... A61B 8/06; A61B 8/065; A61B 8/0883; A61B 8/13; A61B 8/145; A61B 8/463; A61B 8/466; A61B 8/467; A61B 8/469; A61B 8/483; A61B 8/488; A61B 8/5223; A61B 8/523; G01F 1/663; G01S 15/8993; G01S 7/52073; G01S 7/52074; G01S 7/52084
See application file for complete search history.

(56) References Cited

U.S. PATENT DOCUMENTS 6,464,642 B1    10/2002  Kawagishi
6,602,194 B2 *   8/2003  Roundhill ............... A61B 8/14
                                                          600/443
(Continued)

OTHER PUBLICATIONS

Breburda, C.S., et al., "Three-Dimensional Echocardiographic Planimetry of Maximal Regurgitant Orifice Area in Myxomatous Mitral Regurgitation: Intraoperative Comparison With Proximal Flow Convergence," JACC, vol. 32, No. 2, pp. 432-437 (1998).

(Continued)

*Primary Examiner* — Michael T Rozanski

(57) ABSTRACT

A system for presenting multiple parallel slices comprises a display for displaying ultrasound data comprising 3D Doppler data over time. A user interface defines a proximal plane and a distal plane within the ultrasound data that are parallel to one another. The proximal and distal planes define a region of interest (ROI). A signal processor automatically extracts at least two slices based on the ultrasound data within the ROI. The at least two slices are parallel with respect to each other and are displayed on the display.

17 Claims, 5 Drawing Sheets

(51) Int. Cl.
*G01F 1/66* (2006.01)
*G01S 15/89* (2006.01)
*G01S 7/52* (2006.01)
*A61B 8/14* (2006.01)
*A61B 8/08* (2006.01)
*A61B 8/13* (2006.01)

(52) U.S. Cl.
CPC .......... *G01F 1/663* (2013.01); *G01S 7/52073* (2013.01); *G01S 7/52074* (2013.01); *G01S 7/52084* (2013.01); *G01S 15/8993* (2013.01); *A61B 8/13* (2013.01); *A61B 8/467* (2013.01); *A61B 8/483* (2013.01)

(56) References Cited

U.S. PATENT DOCUMENTS 7,404,798 B2 * 7/2008 Kato ................. A61B 5/02007
600/437

2005/0281444 A1 * 12/2005 Lundberg ................. A61B 8/08
382/128
2006/0058651 A1 * 3/2006 Chiao ..................... A61B 8/14
600/437

OTHER PUBLICATIONS

Ge, S., et al., "A Real-time 3-dimensional Digital Doppler Method for Measurement of Flow Rate and Volume Through Mitral Valve in Children: A Validation Study Compared with Magnetic Resonance Imaging," Journal of the American Society of Echocardiography, vol. 18, No. 1, pp. 1-7 (2005).

Picot, P.A., et al., "Three-Dimensional Colour Doppler Imaging," Ultrasound in Med. & Biol., vol. 19, No. 2, pp. 95-104 (1993).

Office Action issued in connection with corresponding DE Application No. 102007020314.6 on May 30, 2017.

* cited by examiner

METHOD AND SYSTEM FOR MEASURING FLOW THROUGH A HEART VALVE

CROSS-REFERENCE TO RELATED APPLICATIONS/INCORPORATION BY REFERENCE

This application is a Continuation of U.S. patent application Ser. No. 11/412,614 entitled, "METHOD AND SYSTEM FOR MEASURING FLOW THROUGH A HEART VALVE", now U.S. Pat. No. 9,612,142 issued on Apr. 4, 2017 and filed Apr. 27, 2006, which is herein incorporated by reference.

BACKGROUND OF THE INVENTION

This invention relates generally to diagnostic ultrasound systems, and more particularly, to method and system for measuring flow through a heart valve.

Diagnosing and assessing regurgitant flow jets within a patient's heart, such as mitral valve or tricuspid valve regurgitation or insufficiency, is challenging with currently available ultrasound systems. The flow patterns are often quite complex with time-varying geometries. Additionally, non-circular orifice areas pose a challenge to visualizing and measuring the flow through the actual orifice area.

When accessing a condition such as Mitral Regurgitation, the size of the regurgitant flow jets may be currently described with the Vena Contracta. The Vena Contracts is defined as the narrowest central flow region of a jet and can be depicted using color flow Doppler. Currently, the proximal isovelocity surface area method (PISA) is used to quantify the size of the flow jet. This method is a planar measurement which makes the assumption that the flow convergence zone is circular and symmetric. Unfortunately, this is seldom the case, and may result in erroneous calculations.

Therefore, a need exists for a method and system for improving the localization of the Vena Contracta to measure the flow through a heart valve. Certain embodiments of the present invention are intended to meet these needs and other objectives that will become apparent from the description and drawings set forth below.

BRIEF DESCRIPTION OF THE INVENTION

In accordance with one embodiment, a system for presenting multiple parallel slices comprises a display for displaying ultrasound data comprising 3D Doppler data over time. A user interface defines a proximal plane and a distal plane within the ultrasound data that are parallel to one another. The proximal and distal planes define a region of interest (ROI). A signal processor automatically extracts at least two slices based on the ultrasound data within the ROI. The at least two slices are parallel with respect to each other and are displayed on the display.

In accordance with another embodiment, a method for displaying multiple parallel slices comprises defining an ROI within a volume of data. The volume of data comprises volumetric color Doppler data over at least one cardiac cycle. At least two slices of ultrasound data are automatically displayed from within the ROI at a first time position. A first flow jet area is calculated on one of the at least two slices at the first time position.

In accordance with another embodiment, a method for measuring a flow jet area over a portion of a cardiac cycle comprises defining an ROI within a volume of data comprising volumetric color Doppler data over at least one cardiac cycle. Multiple parallel slices of ultrasound data from within the ROI are displayed. A flow jet area is measured on a first slice at a first time position and a flow jet area on a second slice is measured at a second time position. The flow jet area is interpolated on the ultrasound data between the first and second time positions.

Figure 1:
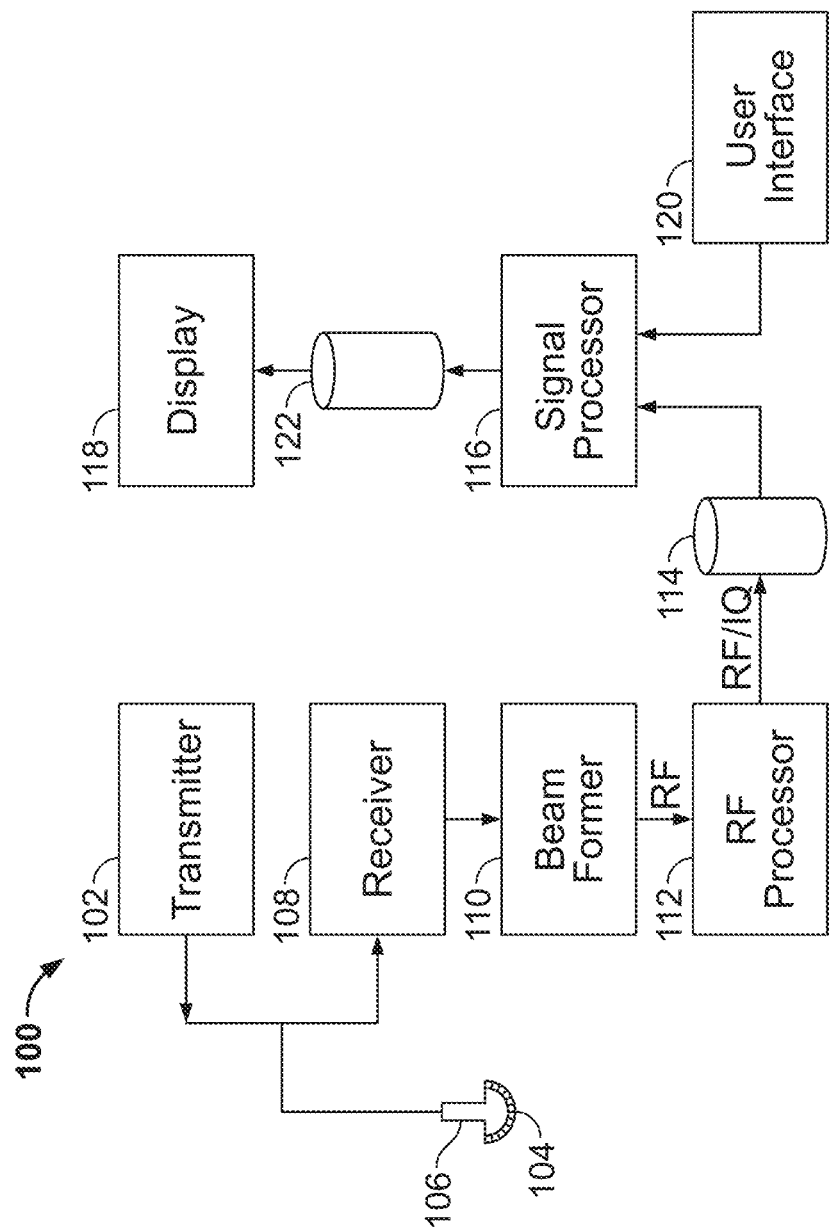
FIG. 1 illustrates a block diagram of an ultrasound system formed in accordance with an embodiment of the present invention.

The foregoing summary, as well as the following detailed description of certain embodiments of the present invention, will be better understood when read in conjunction with the appended drawings. The figures illustrate diagrams of the functional blocks of various embodiments. The functional blocks are not necessarily indicative of the division between hardware circuitry. Thus, for example, one or more of the functional blocks (e.g., processors or memories) may be implemented in a single piece of hardware (e.g., a general purpose signal processor or a block or random access memory, hard disk, or the like). Similarly, the programs may be stand alone programs, may be incorporated as subroutines in an operating system, may be functions in an installed imaging software package, and the like. It should be understood that the various embodiments are not limited to the arrangements and instrumentality shown in the drawings.

DETAILED DESCRIPTION OF THE INVENTION

FIG. 1 illustrates a block diagram of an ultrasound system 100. The ultrasound system 100 includes a transmitter 102 which drives transducers 104 within a probe 106 to emit pulsed ultrasonic signals into a body. A variety of geometries may be used. For example, the probe 106 may be used to acquire 2D, 3D, or 4D ultrasonic data, and may have further capabilities such as 3D beam steering. Other types of probes 106 may be used. The ultrasonic signals are back-scattered from structures in the body, like blood cells or muscular tissue, to produce echoes which return to the transducers 104. The echoes are received by a receiver 108. The received echoes are passed through a beamformer 110, which performs beamforming and outputs an RF signal. The beamformer may also process 2D, 3D and 4D ultrasonic data. The RF signal then passes through an RF processor 112. Alternatively, the RF processor 112 may include a complex demodulator (not shown) that demodulates the RF signal to form IQ data pairs representative of the echo signals. The RF or IQ signal data may then be routed directly to RF/IQ buffer 114 for temporary storage.

The ultrasound system 100 also includes a signal processor 116 to process the acquired ultrasound information (i.e., RF signal data or IQ data pairs) and prepare frames of ultrasound information for display on display 118. The signal processor 116 is adapted to perform one or more processing operations according to a plurality of selectable ultrasound modalities on the acquired ultrasound information. Acquired ultrasound information may be processed in real-time during a scanning session as the echo signals are received. Additionally or alternatively, the ultrasound information may be stored temporarily in RF/IQ buffer 114 during a scanning session and processed in less than real-time in a live or off-line operation. A user interface 120 allows an operator to enter data, enter and change scanning parameters, access protocols, measure structures of interest, and the like. The user interface 120 may be a rotating knob, switch, keyboard keys, mouse, touch screen, light pen, or any other interface device or method known in the art.

The ultrasound system 100 may continuously acquire ultrasound information at a frame rate that exceeds 50 frames per second—the approximate perception rate of the human eye. The acquired ultrasound information is displayed on the display 118. The ultrasound information may be displayed as B-mode images, M-mode, volumes of data (3D), volumes of data over time (4D), or other desired representation. An image buffer 122 is included for storing processed frames of acquired ultrasound information that are not scheduled to be displayed immediately. Preferably, the image buffer 122 is of sufficient capacity to store at least several seconds worth of frames of ultrasound information. The frames of ultrasound information are stored in a manner to facilitate retrieval thereof according to its order or time of acquisition. The image buffer 122 may comprise any known data storage medium.

Figure 2:
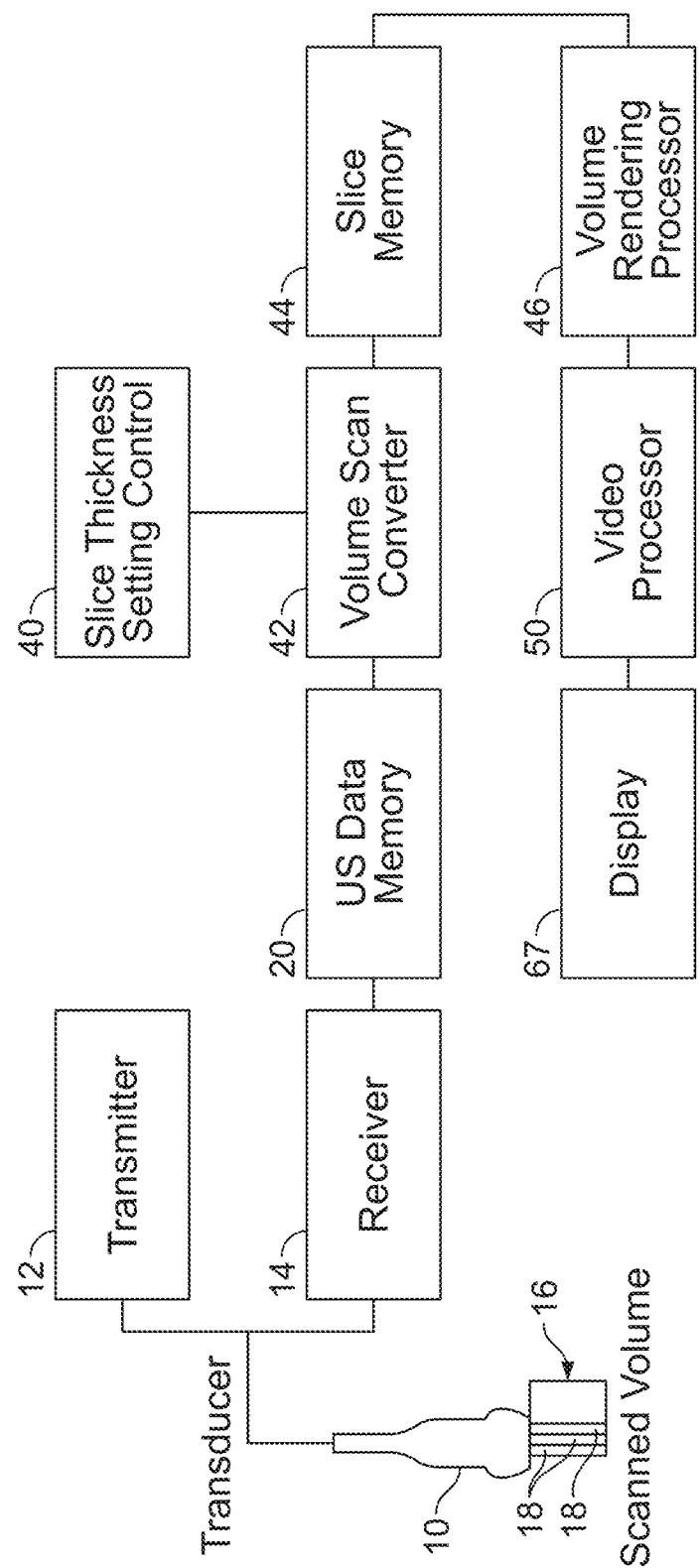
FIG. 2 illustrates a block diagram of an alternative ultrasound system formed in accordance with one embodiment of the present invention.

FIG. 2 illustrates an alternative ultrasound system. The system includes a probe 10 connected to a transmitter 12 and a receiver 14. The probe 10 transmits ultrasonic pulses and receives echoes from structures inside of a scanned ultrasound volume 16. Memory 20 stores ultrasound data from the receiver 14 derived from the scanned ultrasound volume 16. The volume 16 may be obtained by various techniques (e.g. 3D scanning, real-time 3D imaging or 4D scanning, volume scanning, 2D scanning with transducers having positioning sensors, freehand scanning using a Voxel correlation technique, 2D or matrix array transducers and the like).

The probe 10 may be moved, such as along a linear or arcuate path, while scanning a region of interest (ROI). At each linear or arcuate position, the probe 10 obtains scan planes 18. The scan planes 18 are collected for a thickness, such as from a group or set of adjacent scan planes 18. The scan planes 18 are stored in the memory 20, and then passed to a volume scan converter 42. In some embodiments, the probe 10 may obtain lines instead of the scan planes 18, and the memory 20 may store lines obtained by the probe 10 rather than the scan planes 18. The volume scan converter 42 may store lines obtained by the probe 10 rather than the scan planes 18. The volume scan converter 42 receives a slice thickness setting from a slice thickness setting control 40, which identifies the thickness of a slice to be created from the scan planes 18. The volume scan converter 42 creates a data slice from multiple adjacent scan planes 18. The number of adjacent scan planes 18 that are obtained to form each data slice is dependent upon the thickness selected by slice thickness setting control 40. The data slice is stored in slice memory 44 and is accessed by a volume rendering processor 46. The volume rendering processor 46 performs volume rendering upon the data slice. The output of the volume rendering processor 46 is passed to the video processor 50 and display 67.

The position of each echo signal sample (Voxel) is defined in terms of geometrical accuracy (i.e., the distance from one Voxel to the next) and ultrasonic response (and derived values from the ultrasonic response). Suitable ultrasonic responses include gray scale values, color flow values, and angio or power Doppler information.

Figure 3:
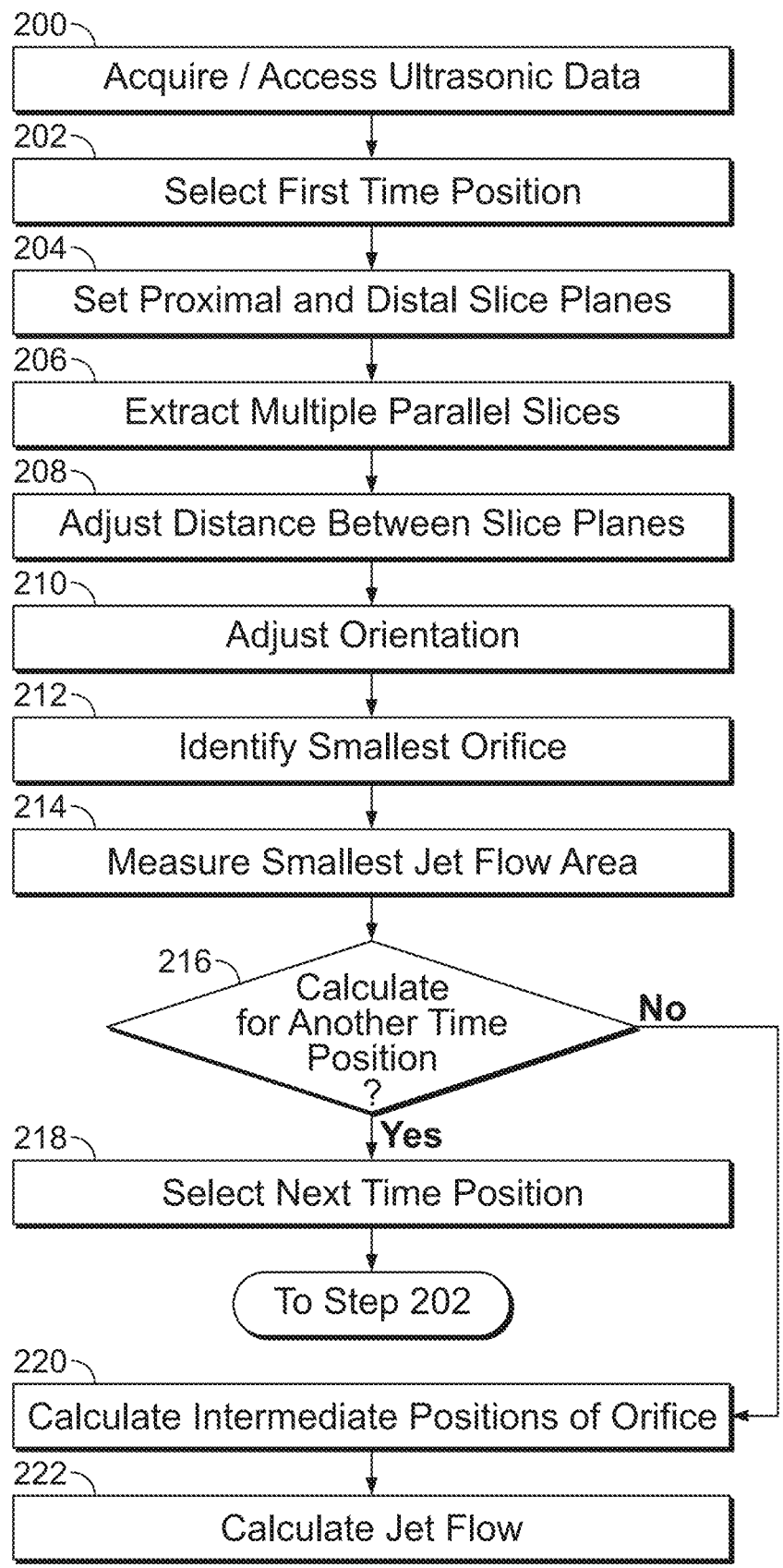
FIG. 3 illustrates a method for locating and measuring a flow jet within the heart in accordance with an embodiment of the present invention.

FIG. 3 illustrates a method for locating and measuring a flow jet within the heart. The following example is directed to measuring the Vena Contracta which is used when evaluating Mitral Regurgitation. In step 200, ultrasound data is acquired of at least a portion of a patient's heart to image the structure of interest. For example, the ultrasound data used to measure the Vena Contracta may include data representative of the mitral valve. The ultrasound data may be a volume of data comprising 3D color Doppler data over time, such as over one or more heart cycles, and may be stored in the memory 20. Alternatively, ultrasound data which has been previously acquired and stored in the memory 20 may be accessed for processing.

Figure 4:
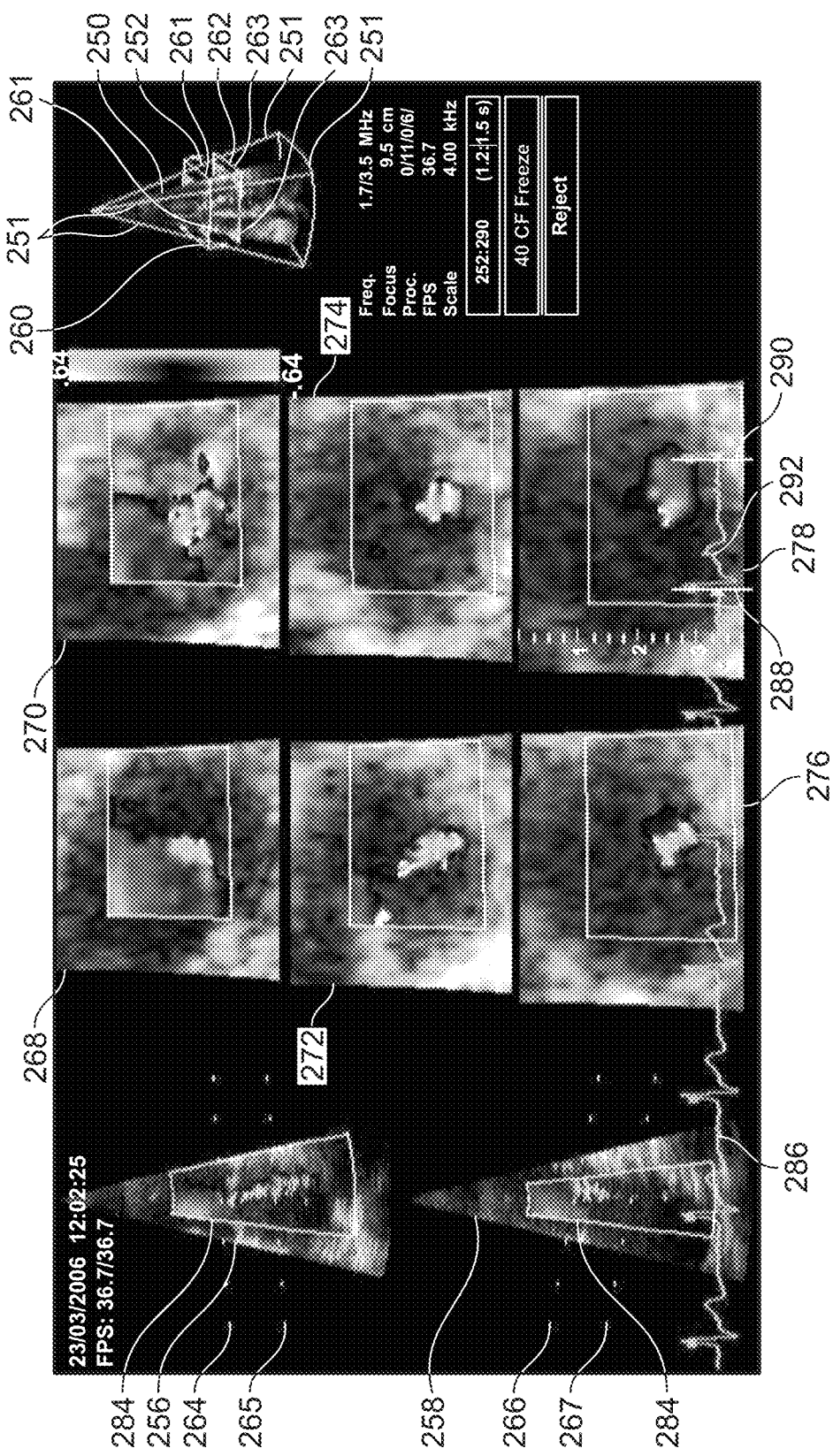
FIG. 4 illustrates ultrasound images displayed on the display in accordance with an embodiment of the present invention.

FIG. 4 illustrates ultrasound images displayed on the display 118. A representation of the volume of data 250 acquired and/or accessed in step 200 is illustrated with a plurality of edge lines 251 defining a wireframe, as well as an associated ECG trace 286. Boundary lines 288 and 290 on the ECG trace 286 indicate the heart cycle being processed.

In step 202, a first time position is selected by the operator. For example, the Vena Contracta for Mitral Regurgitation is typically measured during the systole phase of the heart cycle. The operator may scroll a time position indicator 292 through the ECG trace 286 to select the first time position. Alternatively, the signal processor 116 may automatically detect and position the time position indicator 292 at the first time position. The operator may then adjust the time position indicator 292 after automatic positioning by the signal processor 116. It should be understood that a stand-alone computer or other processor may be used to implement the functions of FIG. 3 in place of a signal processor 116 which may be integrated with an ultrasound scanner. Further, the program instructions for implementing the functions of FIG. 3 may be stored on various media devices known in the art.

In step 204, the operator uses the user interface 120 to define an effective region of interest (ROI) 252 around the structure or orifice of interest. For example, the operator may set a top or proximal slice plane 260 at a first depth above the mitral valve or other anatomy of interest and a bottom or distal slice plane 262 at a second depth below the mitral valve to define the ROI 252. The proximal and distal slice planes 262 and 264 are parallel with respect to each other. Alternatively, the signal processor 116 may set the proximal and distal slice planes 260 and 262 based on predetermined or average patient data, or at preset depths. The operator may then adjust the locations of the proximal and distal slice planes 260 and 262. Optionally, for ease of anatomical inspection while defining the ROI 252, the operator may temporarily remove or turn off the color Doppler information so that only the tissue structures are displayed. In steps where the flow jet is visualized and/or measured, the color Doppler information may be turned on.

Also, the operator may change the color parameters to change how the color is interpreted and displayed.

One or more long-axis planes may also be displayed on the display 118 to guide the positioning of the proximal and distal slice planes 260 and 262. In FIG. 4, a first long-axis plane 256 may show the main probe plane, or the azimuth plane, while a second long-axis plane 258 may show a plane at 90 degrees to the first long-axis plane 256. A Doppler ROI 284 defined during the acquisition of the ultrasound data is illustrated, and the color Doppler data is calculated for ultrasound data within the Doppler ROI 284. The positions of the proximal and the distal slice planes 260 and 262 are illustrated with first and second dotted lines 264 and 265, respectively, on the first long-axis plane 256 and with first and second dotted lines 266 and 267, respectively, on the second long-axis plane 258. Additionally, the position of the proximal slice plane 260 is illustrated with first edge lines 261 on the representation of volume data 250. And the position of the distal slice plane 262 is illustrated with second edge lines 263 on the representation of the volume data 250. Other indicators may be used. Alternatively, three long-axis planes which are 60 degrees apart with respect to each other may display standard 2D echocardiography scanning planes with the proximal and distal slice planes 260 and 262 indicated thereon.

In step 206, the volume scan converter 42 extracts multiple parallel slices from ultrasound data selected by the ROI 252. By way of example, two, four or six parallel slices may be extracted and displayed, although the operator may select to have more or a different number of parallel slices extracted. In one embodiment, the parallel slices may be parallel c-scan slices. In another embodiment, the parallel slices may be positioned non-orthogonal with respect to a central vector of the volumetric ultrasound scan. In another embodiment, the position of one or more of the parallel slices may be interpolated.

Figure 5:
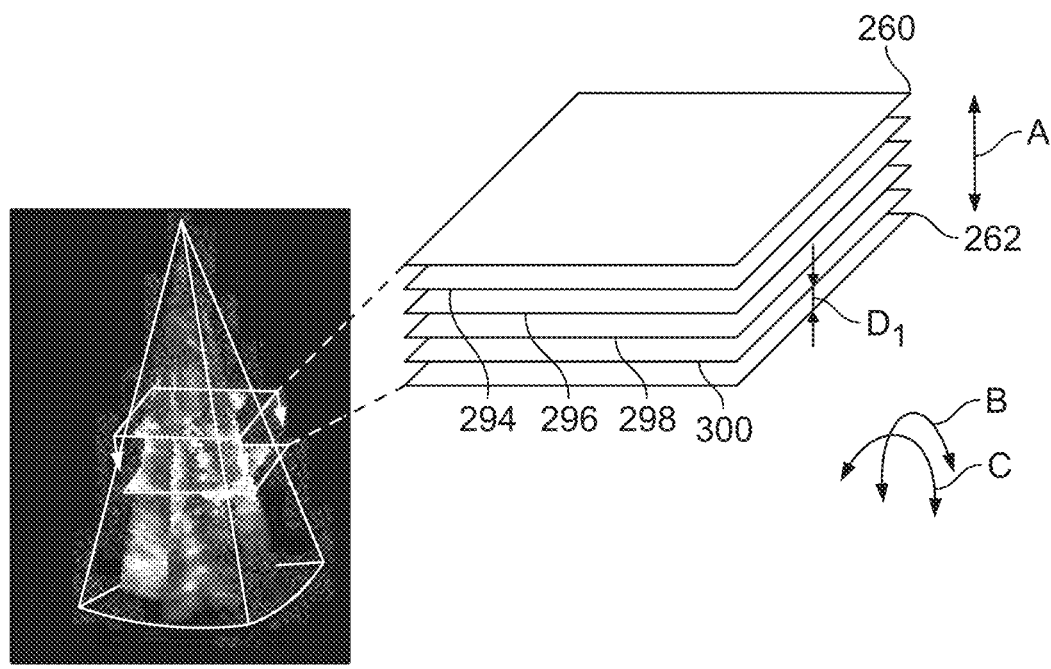
FIG. 5 illustrates multiple parallel slices extracted from the ROI in accordance with an embodiment of the present invention.

FIG. 5 illustrates multiple parallel slices extracted from the ROI 252. The proximal and distal slice planes 260 and 262 are illustrated with first, second, third and fourth intermediate slice planes 294, 296, 298 and 300. First, second, third, fourth, fifth and sixth slices 268, 270, 272, 274, 276 and 278 are displayed on the display 118 of FIG. 4 in a tiled or grid format including a plurality of columns and rows. The first slice 268 corresponds to the proximal slice plane 260 and the sixth slice 278 corresponds to the distal slice plane 262, while the first through fourth intermediate slice planes 294-300 correspond to the second through fifth slices 270-276, respectively.

Distance D1 between each of the adjacent slice planes 260, 294-300 and 262 is the same, and thus the first through sixth slices 268-278 are positioned equidistant relative to one another. Each of the first through sixth slices 268-278 may have the same predetermined thickness. Alternatively, the operator may change the thickness of the first through sixth slices 268-278 with the slice thickness setting control 40.

In step 208, the operator may adjust the distance D1 between the slice planes 260, 294-300 and 262 along the direction of arrow A (FIG. 5), which also adjusts the size of the ROI 252. For example, the operator may move one or more of the first and second lines 264 and 265 displayed on the first long-axis plane 256 and first and second lines 266 and 267 displayed on the second long-axis plane 258. The depth of each of the proximal and distal slice planes 260 and 262 may be changed independently. If the proximal slice plane 260 is moved upwards towards the surface of the probe 106, the distal slice plane 262 may remain in its current location while the first through fourth intermediate slice planes 294-300 are adjusted to maintain the equidistant relationships with respect to each other and the proximal and distal slice planes 260 and 262. The first through sixth slices 268-280, position of the ROI 252, as well as other effected indicators, are updated on the display 118 to reflect the current slice information and location.

In step 210, the operator may adjust the orientation of the slice planes 260, 294-300 and 262 so that the flow jet runs perpendicular to the planes as illustrated by viewing the first through sixth slices 268-278 on the display 118. The orientation adjustment may be accomplished by adjusting one or more of the first and second lines 264 and 265 on the first long-axis plane 256 and the first and second lines 266 and 267 displayed on the second long-axis plane 258 with the user interface 120. The orientation adjustment moves the proximal and distal slice planes 260 and 262 and the first through fourth intermediate slice planes 294-300 in unison, maintaining the equidistant relationship between them. The slice planes 260, 262 and 294-300 may be adjusted in any direction, such as front to back and side to side as illustrated with arrows B and C on FIG. 5. The orientation adjustment is not limited to these directions, however, and the slice planes 260, 262 and 294-300 may be adjusted in any combination of directions. As the orientation of the slice planes 260, 262 and 294-300 is adjusted, the first through sixth slices 268-278 are updated on the display 118 to reflect the current position. The first and second lines 264 and 265, and 266 and 267, position of the ROI 252, as well as other effected indicators, are updated on the display 118 to reflect the current slice information and location.

The steps 208 and 210 may be iterative, that is, the operator may adjust the position and orientation of the slice planes 260, 262 and 294-300 multiple times to find the best possible location and orientation to measure the flow jet of interest. In step 212, the operator may visually identify the smallest orifice on one of the first through sixth slices 268-278, which corresponds to the smallest flow jet area. In this example, the smallest flow jet area is the Vena Contracta.

Figure 6:
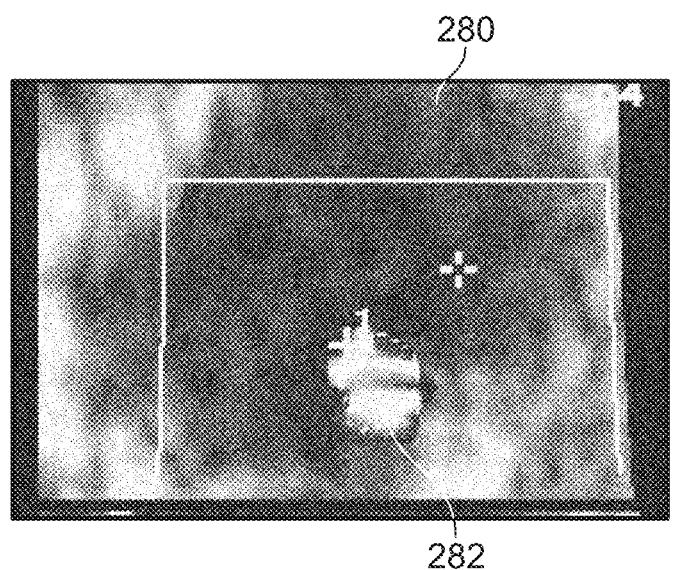
FIG. 6 illustrates an example of measuring the Vena Contracta area on one of the multiple parallel slices in accordance with an embodiment of the present invention.

In step 214, the area of the smallest orifice, or the Vena Contracta area, is measured on the slice identified in step 212. FIG. 6 illustrates an example of measuring the Vena Contracta area on a slice 280. In one embodiment, the operator may use the user interface 120 to trace an area 282 or use a caliper to measure a diameter of the Vena Contracta area. Alternatively, the operator may define or select one or more points and the signal processor 116 may detect the Vena Contracta area using an edge detecting or boundary defining algorithm. Optionally, the operator may choose to measure the Vena Contracta area on more than one slice at the same time position within the heart cycle to identify the smallest orifice area.

The position of the Vena Contracta moves during the cardiac cycle due to the movement of the atrioventricular (AV) plane. Therefore, in step 216, if the operator chooses to measure the Vena Contracta area at an additional time position within the cardiac cycle, flow passes to step 218 where the operator selects a next time position, which may be before or after the first time position and may be within the systole phase of the heart cycle. Optionally, the signal processor 116 may automatically select the next time position and allow the operator to adjust or change the next time position. By selecting at least two different time positions within the heart cycle, the structure of interest is automatically tracked on the slices over a portion or all of the cardiac cycle. The method then returns to step 204 to set and adjust the scan planes and measure the flow jet area at the next time position.

Returning to step 216, if no more calculations are to be done, the method flows to step 220. In step 220, the signal processor 116 calculates intermediate positions of the Vena Contracta by interpolating between the points identified for the first, next and/or subsequent time positions. This calculation thus provides an automatic tracking of the position of the Vena Contracta. If a single time position is used, the identified data may be interpolated over the systole phase or other phase portion(s) of the cardiac cycle, or for a predetermined time period before, after or surrounding the first time position. In step 222, the signal processor 116 measures the size of the orifice or the Vena Contracta on the multiple slice planes over time based on the volumetric color Doppler data.

The measurement of the Vena Contracta may be more fully automated by indicating, on a first parallel slice at a first position, the area of interest. This may be done by drawing an ROI or by selecting one or more points and then automatically detecting the area with the signal processor 116. The signal processor 116 may then detect the direction of blood flow within the ROI to define the position for the slice plane relative to the probe 106. The area may then be automatically calculated, either between the first position and an identified second position, or automatically with respect to position(s) adjacent to the first position as discussed previously.

A technical effect is using the ultrasound data to calculate the Vena Contracta area or other identified structure within the heart over time. The automated tracking of the anatomical structure in the slice positions over all or portions of the cardiac cycle allow for an accurate measurement of the flow jet. Therefore, as the size, shape and/or position of the orifice may change, the Vena Contracta can be automatically tracked and measured from multiple slices based on the volumetric color Doppler data.

While the invention has been described in terms of various specific embodiments, those skilled in the art will recognize that the invention can be practiced with modification within the spirit and scope of the claims.

What is claimed is:

1. A system for presenting multiple parallel slices, comprising:
   a display for displaying ultrasound data acquired from a scanned ultrasound volume;
   a user interface for selecting a first slice plane within the ultrasound data; and
   a signal processor configured to:
   display a plurality of parallel slices extracted from the ultrasound data, where the plurality of parallel slices corresponds to a plurality of slice planes in the scanned ultrasound volume and one of the plurality of slice planes is the first slice plane, wherein the plurality of slice planes are parallel to each other and are positioned equidistant with respect to one another, and wherein the plurality of slice planes comprises at least three slice planes;
   display a B-mode image with a first line superimposed on the B-mode image, wherein the first line represents a position of the first slice plane with respect to the B-mode image;
   display a representation of the first slice plane superimposed on a representation of the volume at a position and orientation from which the first slice plane was extracted, wherein the signal processor is further configured to simultaneously display the plurality of parallel slices, the B-mode image with the superimposed first line, and the representation of the first slice plane superimposed on the representation of the volume; and
   wherein the user interface is configured to adjust an orientation of the plurality of parallel slice planes with respect to the scanned ultrasound volume, wherein the plurality of parallel slice planes remain parallel to each other after the orientation is adjusted.

2. The system of claim 1, wherein the user interface is configured to adjust at least one of a distance between each of the plurality of slice planes and a number of the plurality of parallel slices extracted from the ultrasound data.

3. The system of claim 1, wherein the user interface is configured to adjust the thickness of each of the plurality of parallel slices.

4. The system of claim 1, where the B-mode image is a long-axis plane.

5. The system of claim 1, wherein the signal processor is further configured to display the B-mode image with a second line superimposed on the B-mode image at the same time as the first line, wherein the second line represents a position of a second one of the plurality of slice planes with respect to the B-mode image.

6. The system of claim 1, wherein the plurality of parallel slices are displayed in a first region of the display; the B-mode image with the first line superimposed on the B-mode image is displayed in a second region of the display; and the representation of the first slice plane superimposed on the representation of the volume is displayed on a third region of the display; wherein the first, second, and third regions of the display are non-overlapping.

7. The system of claim 1, wherein the signal processor is configured to display the first line as a first dotted line.

8. The system of claim 1, wherein the representation of the volume is a wireframe.

9. The system of claim 1, wherein the signal processor is configured to display the plurality of parallel slices in a tiled format comprising a plurality of rows and a plurality of columns.

10. The system of claim 1, wherein the user interface is configured to adjust the orientation of the plurality of parallel slice planes with respect to the scanned ultrasound volume in response to an input through a rotating knob.

11. A method for displaying multiple parallel slices, comprising:
    accessing ultrasound data acquired from a scanned ultrasound volume;
    selecting a first slice plane within the ultrasound data with a user interface;
    extracting and displaying on a first region of a display a plurality of parallel slices from the ultrasound data, wherein the plurality of parallel slices corresponds to a plurality of slice planes in the scanned ultrasound volume and one of the plurality of slice planes is the first slice plane, wherein the plurality of slice planes are parallel to each other and are positioned equidistant with respect to one another, and wherein the plurality of slice planes comprises at least three slice planes;
    displaying a B-mode image with a first line superimposed on the B-mode image on a second region of the display, wherein the first line represents a position of the first slice plane with respect to the B-mode image;
    displaying a representation of the first slice plane superimposed on a representation of the volume at a position and orientation from which the first slice plane was extracted, wherein the first slice plane superimposed on the representation of the volume is displayed on a third region of the display;

wherein the plurality of parallel slices, the B-mode image with the superimposed first line, and the representation of the first slice plane superimposed on the representation of the volume are all displayed simultaneously; and adjusting with the user interface an orientation of the plurality of parallel slice planes with respect to the scanned ultrasound volume, wherein the plurality of parallel slice planes remain parallel to each other after said adjusting the orientation.

12. The method of claim 11, further comprising adjusting with the user interface at least one of a distance between each of the plurality of slice planes and a number of the plurality of slice planes.

13. The method of claim 12, wherein adjusting with the user interface at least one of a distance between each of the plurality of slice planes and a number of the plurality of parallel slices extracted from the ultrasound data is in response to a first input through a first rotating knob.

14. The method of claim 11, wherein the B-mode image is a long-axis plane.

15. The method of claim 11, further comprising displaying a plurality of lines superimposed on the B-mode image, wherein one of the plurality of lines is the first line.

16. The method of claim 11, wherein the representation of the volume is a wireframe.

17. The method of claim 11, wherein the plurality of parallel slices is displayed in the first region in a tiled format comprising a plurality of rows and a plurality of columns.

* * * * *